United States Patent [19]

Carter

[11] Patent Number: 5,006,071
[45] Date of Patent: Apr. 9, 1991

[54] TECHNIQUE FOR THE PREVENTION OF ALVEOLAR OSTEITIS

[76] Inventor: Dewey G. Carter, 3002 Tanbark Ct., Burlington, N.C. 27215

[21] Appl. No.: 191,413

[22] Filed: May 9, 1988

[51] Int. Cl.$^5$ ............................................. A61C 5/00
[52] U.S. Cl. .................... 433/215; 424/435; 424/426
[58] Field of Search ............. 433/215, 138; 424/435, 424/426, 427, 428, 423; 604/358

[56] References Cited

U.S. PATENT DOCUMENTS

| | | | |
|---|---|---|---|
| 3,919,773 | 11/1975 | Freeman | 433/201.1 |
| 3,952,414 | 4/1976 | Shovers | 433/173 |
| 4,186,448 | 2/1980 | Brekke | 128/92 YG |
| 4,357,935 | 11/1982 | Frantzich et al. | 128/156 |
| 4,642,230 | 2/1987 | Whitehead et al. | 604/890.1 |
| 4,677,139 | 6/1987 | Feinmann et al. | 128/90 |
| 4,804,688 | 2/1989 | Vassileff | 524/2 |

OTHER PUBLICATIONS

Quinn, Peter and Tidewell, Otto: Update: J. Oral Maxill of AC. Surg.-vol. 3, No. 6 (Jun. 1987).
Bahn, S. L.: Plaster: A Bone Substitute, Oral Surg. Oral Med. & Oral Path. 21: 672–681 (May 1966).
Labourg, L. and Biou, C.: The Embedding of Plaster of Paris in Surgical Cavities of the Jaws, Sem. Hop. Paris 37: 1195–1197, 1961.
Bier, S. J.: Plaster of Paris: A Periodontal Surgical Dressing, N.Y. State D. J. 36: 347–352, Jun.-Jul. 1970.
Frame, J. W., Route, P. G. J., and Browne, R. M.: Rodge Augmentation Using Solid and Porous Hydroxylapatite Particles With and Without Autogenous Bone or Plaster: J. Oral Maxillofac. Surg. 45: 771–777, 1987.

Primary Examiner—John J. Wilson
Attorney, Agent, or Firm—Rhodes, Coats & Bennett

[57] ABSTRACT

A moldable, absorbable dressing and method for the prevention of alveolar osteitis following the extraction of a tooth or removal of a cyst. The dressing is primarily plaster of Paris with approximately 5 wt. % of tetracycline and 0.01 wt. % of hydrocortisone added to reduce inflammation at the wound site. The plaster of Paris may include 0.85 wt. % $K_2SO_4$ to facilitate solidification in the body. The method includes mixing the plaster of Paris with water to form a semi-liquid paste of plaster of Paris. A plug of absorbable, gelatin sponge is then cut out slightly larger than the cavity left by the tooth extraction or cyst removal. The sponge is immersed into the semi-liquid plaster to absorb as much of the plaster as possible. The impregnated sponge is then compressed slightly and placed in the cavity. The gelatin sponge is somewhat resilient which aids in filling the socket as it expands. A small amount of plaster is added to the exposed upper surface of the sponge to seal its surface. The tissue above the plaster impregnated sponge are then sutured together to enclose it completely, thus preventing any food or debris from entering the wound site. As the cavity heals, the dressing is absorbed and permits regeneration of bone in the socket.

16 Claims, 1 Drawing Sheet

TECHNIQUE FOR THE PREVENTION OF ALVEOLAR OSTEITIS

BACKGROUND OF THE INVENTION

1. Field of the Invention

The present invention relates in general to surgical dressings and, in particular, to a dressing for the prevention of alveolar osteitis following the removal of a tooth or cyst.

2. Description of the Prior Art

Development of alveolar osteitis, commonly known as dry socket, following the removal of a tooth or maxillary cyst is a well known phenomena. Symptoms which usually accompany a dry socket include a severe pounding and throbbing pain that is generally unrelenting and usually begins within forty-eight to seventy-two hours after the surgery. A dry socket is most likely to occur with the surgical removal of impacted teeth, and in particular, with the removal of the mandibular third molars. It has been estimated that between ten and forty percent of all such extractions eventually develop a dry socket.

Currently the accepted procedure to aid in the prevention of a dry socket includes minimizing unnecessary trauma during surgery, irrigating the extraction site following surgery with a saline solution, use an antibiotic dressing following extraction, and avoiding vasoconstrictors, such as infiltration anesthesia. If a dry socket still occurs, the accepted treatment includes irrigation of the extraction site with a saline solution to flush debris out the extraction site, placement of a socket dressing using a medicated iodoform gauze, for example Bipp's Paste, changing the dressing every twenty-four to forty-eight hours until symptoms abate, and, on occasion, prescription of a broad spectrum antibiotic. Because of the severe pain associated with a dry socket, nerve block anesthesia may be required to properly place the dressing.

Generally, it is believed that the syndrome consists of a blood clot forming and then subsequently being lost between the third and fifth day following surgery. It has also been theorized that this premature dislodgment of the blood clot may be due to either physical dislodgment, lack of proliferation of capillary buds into the blood clot, or a chemical lysis of the blood clot. Regardless of its cause, dry socket is a prevalent and painful condition.

U.S. Pat. No. 3,952,414 to Shovers et al, discloses a method for the prevention of osteitis and for the prevention of atrophy of alveolar bone which consists of embedding an implant into the bony cavity, such as a cystic cavity or alveolus after tooth extraction. The preformed implant is a solid body of tissue-compatible material and has a smooth unbroken exterior surface defining a bulbous, gibbous shape which generally follows the contour of the cavity. In one application, the implant is placed in the extraction socket following the removal of the tooth. The size and placement of the implant are chosen to be sufficient to locate the occlusal end of the implant approximately three to four millimeters beneath the height of the bony tissue. The normal healing processes are said to be adequate to entirely surround the implant with trabecular bone tissue and to form an occlusal layer of boney tissue above the implant, similar to steel reinforced concrete. However, the implant is not absorbed by the body over time and is not moldable to minimize pressure at the affected site.

U.S. Pat. No. 3,919,773 to Freeman discloses a dental implant composition and placement method which includes a moldable, polymerizable material which is inserted into the tooth socket immediately after the tooth has been extracted. Being moldable, the material conforms to and substantially fills the socket. Prior to inserting the moldable material into the socket, the surface of the material is first coated or dusted with particulate calcium sulfate which becomes embedded in the outer surface of the moldable material. The calcium sulfate is dissolvable in body fluids so that eventually minute voids develop in the outer surface of the hardened implant. These voids are said to promote tissue attachment to firmly anchor the implant. However, the implant is not absorbed by the body and it is intended as an anchor for subsequent attachment of a crown or other appliance and is not directed at preventing the occurrence of a dry socket.

Previously, a number of materials have been used to help correct various types of bone defects. For example, plaster of Paris has been considered as a material to fill defects in bone or as a bone substitute since the late 1800's. The plaster usually is completely absorbed by the body and normal bone fills the cavity with only a slight reaction to the plaster of Paris. Plaster of Paris implants are known to be the most quickly absorbed of most implants taking on an average 4.7 weeks. In contrast, autogenous bone implants require approximately seven weeks to be absorbed. Liquid plaster is normally used to fill the defect. Where indicated, an oral antibiotic can be incorporated directly into the plaster of Paris which acts as a medicinal vehicle. As the plaster of Paris is absorbed by the body, the antibiotic granules can be released. An extensive review of plaster of Paris as a bone substitute is reported by Bahn S. L.:Plaster: A Bone Substitute. *Oral Surg., Oral Med.* and *Oral Path.* 21: 672–681 (May) 1966.

Labourg and Biou were the first to report using plaster of Paris to fill the wounds remaining after odontectomy of impacted third molars as well as other osseous defects in the mandible and maxilla. Labourg and Biou first formed plugs of plaster of Paris of various size and then utilized the plug that best fit the size of the bony cavity to fill the extraction site or cystic pocket. The plaster of Paris plug was shaped to the form of the bony cavity using the same instruments as used for a bone graft to make the filling as complete as possible. Tissue above the filled cavity was then closed by making deep points to draw together and hold the tissues in place. Labourg and Biou noted that the tolerance of plaster was very good and that the plaster is absorbed within three or four weeks as shown by clinical examination and by x-ray (Labourg. L. and Biou, C.: The Embedding of Plaster of Paris in Surgical Cavities of the Jaws, *Sem. Hop. Paris* 37: 1195–1197, 1961). However, their implant was not moldable to minimize pressure at the affected site and was not directed at preventing the occurrence of a dry socket.

Plaster of Paris also has been used as a periodontal surgical dressing (Bier, S. J.: Plaster of Paris: A Periodontal Surgical Dressing, *N.Y. State D. J.* 36: 347–352 (June–July) 1970). Bier noted that the presence of plaster of Paris in the defect apparently discourages a rapid downgrowth of epithelium and permits connective tissue regeneration. Bier also noted that none of the cases under study demonstrated postoperative pain, swelling, or secondary infection. Bier believed that a space filler, such as the plaster, facilitates regeneration by helping to form a healthy clot. Thus, the risk of granulation tissue breakdown or necrosis and delayed healing may be decreased by the use of space-occupying material to restrict the primary hematoma to the periphery of the lesion. However, the plaster was only intended as temporary space filler and was not directed at preventing the occurrence of a dry socket. In addition, it is believed that Bier's composition would be absorbed by the body too quickly to permit regeneration of bone in the affected area.

Plaster of Paris also has been used with solid and porous hydroxylapatite particles as a medicinal vehicle to faciliate manipulation of the hydroxylapatite particles during placement on the alveolar ridge and as a means of limiting their initial migration (Frame, J. W., Rout, P. G. J., and Browne, R. M.: Ridge Argumentation Using Solid and Porous Hydroxylapatite Particles with and Without Autogenous Bone or Plaster: *J. Oral Maxillofac. Surg.* 45: 771-777, 1987). However, the plaster was only intended as a temporary medicinal vehicle to aid in the construction of the denture bearing surface and was not directed at preventing the occurrence of a dry socket.

It has thus become desirable to develop a composition and method for preventing the occurrence of dry socket, which at the same time, is moldable to prevent unnecessary pressure at the affected site and is absorbed into the body to permit regeneration of bone in the affected area.

SUMMARY OF THE INVENTION

The present invention solves the aforementioned problems associated with the prior art by providing a method and composition for preventing dry socket. The moldable, absorbable composition is primarily plaster of Paris with 5 wt. % of tetracycline and 0.01 wt. % of hydrocortisone added to reduce inflammation at the wound site. The plaster of Paris may include 0.85 wt. % $K_2SO_4$ to facilitate setting up in the human body. The method includes mixing approximately 1 gram of plaster of Paris with 0.1 ml. of water to form a semi-liquid paste of plaster of Paris. A plug of absorbable, gelatin sponge is then cut out slightly larger than the cavity left by the tooth extraction. The sponge is immersed into the semi-liquid plaster to absorb as much of the plaster as possible. The impregnated sponge is then compressed slightly and placed in the cavity. The gelatin sponge is somewhat resilient which aids in filling the cavity as it expands. A small amount of plaster is added to the exposed upper surface of the sponge to seal its surface. The tissues above the plaster impregnated sponge are then sutured together to enclose it completely, thus preventing any food or debris from entering the wound site.

In addition to being somewhat resilient which aids in filling the cavity, the gelatin sponge both reduces the amount of plaster required and, since the gelatin is more quickly absorbed by the body than the plaster, allows vascular ingrowth into the remaining plaster. This minimizes the opportunity for portions of the plaster to remain unabsorbed.

Small wounds may not need the gelatin sponge. In such cases the semi-liquid plaster is allowed to stand for 1 or 2 minutes in order to form a putty-like consistency. The putty-like, plaster of Paris is then used to fill the cavity formed by the extraction of a tooth or removal of a cyst. After the cavity is filled, approximately 1 or 2 minutes allows the plaster to further cure and solidify in place prior to suturing.

The method and composition of the present invention is operable to prevent the occurrence of the painful condition known as dry socket and, at the same time, is moldable to prevent unnecessary pressure at the affected site and is absorbed into the human body to permit regeneration of bone in the affected area.

Accordingly, one aspect of the present invention is to provide a method and composition for the prevention of dry socket.

Another aspect of the present invention is to provide a composition for the prevention of dry socket which is easily moldable, thereby preventing pressure at the affected site.

Still another aspect of the present invention is to provide a composition for the prevention of dry socket which is readily absorbed into the body to permit regeneration of bone in the affected area.

These and other aspects of the present invention will be more clearly understood after a review of the following description of the preferred embodiment of the invention.

DESCRIPTION OF THE PREFERRED EMBODIMENT(S)

The present invention comprises a formulation for use as prevention of post-extraction aveolitis, commonly known as dry socket. The dressing composition is primarily plaster of Paris which is packed into the extraction site. There is no need to remove or replace the dressing since it is absorbed by the body as granulation tissue, formed during the healing of the tooth socket, replaces the composition. By the time healing is complete, the dressing has substantially disappeared.

The invention is based on the surprising discovery that plaster of Paris, when packed into the cavity left by tooth extraction or removal of a cyst, prevents the occurrence of the painful condition known as dry socket. Also, because the plaster of Paris is used in a semi-liquid form, it is readily moldable into the wound opening left by the surgery. Thus, there is little, if any, pain as a result of physical pressure on the wound site. In addition, the composition of plaster of Paris is absorbed by the body over a period of 6½ to 7 weeks. Finally, even when used alone, the plaster of Paris usually causes little or no inflammation at the wound site. In the preferred embodiment, the addition of 2 to 5 wt. % of tetracycline and 0.01 to 0.05 wt. % of hydrocortisone serves to further minimize inflammation in the area of the wound.

Specifically, the preferred form of the composition consists of:

| Ingredients | Amount |
| --- | --- |
| plaster of Paris ($2CaSO_4.H_2O$) | 99.15 wt. % |
| $K_2SO_4$ | 0.85 wt. % |
| tetracycline | 2 to 5 wt. % of plaster |
| hydrocortisone | 0.01 to 0.05 wt. % of plaster |

One gram of the above dry composition is mixed with approximately 0.1 ml. of sterilized water to make a semi-liquid paste just before treatment is begun. These amounts need not be exact to represent a preferred form of the composition. In the preferred embodiment, the plaster of Paris is sterilized, medical grade plaster which already contains $K_2SO_4$ to aid the solidification of the plaster in the human body and is available from the United States Gypsum Company, Chicago, Ill. The tetracycline and hydrocortisone are added to reduce inflammation which sometimes occurs at the wound site.

Figure 1:
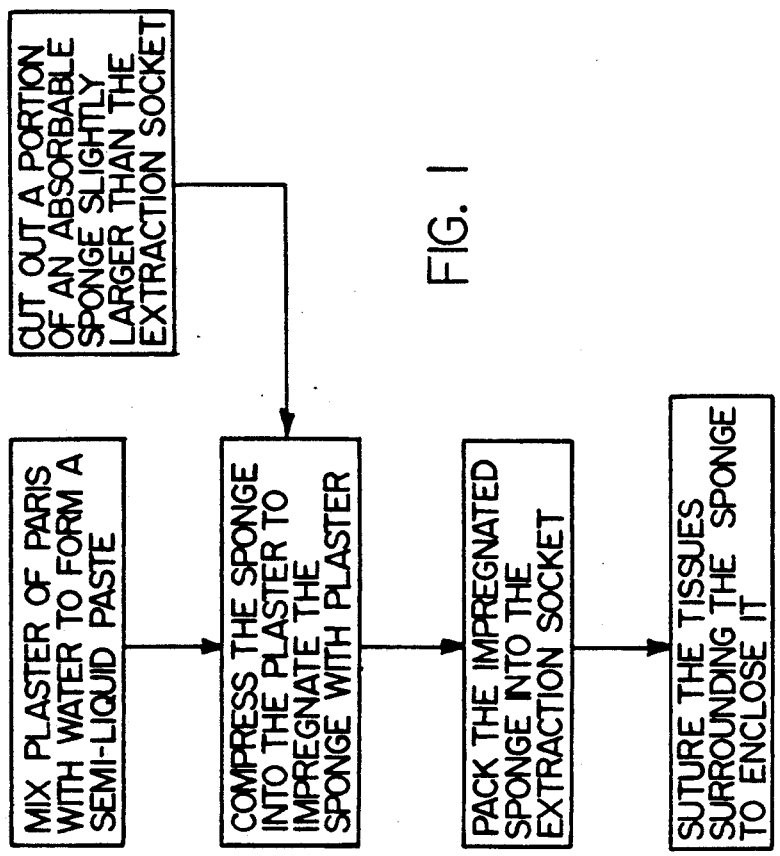
FIG. 1 is a diagramatic representation of the process of the present invention.

Turning to FIG. 1, the steps of the present invention include mixing approximately 1 gram of plaster of Paris with 0.1 ml. of water to form a semi-liquid paste of plaster of Paris. A plug of absorbable, gelatin sponge is then cut out slightly larger than the cavity left by the tooth extraction. The sponge is immersed into the semi-liquid plaster to absorb as much of the plaster as possible. A suitable sponge is available from the Upjohn Company, Kalamazoo, Mich., as Gelfoam ™ sterile sponge. The impregnated sponge is then compressed slightly and packed into the cavity. The gelatin sponge is somewhat resilient which aids in filling the cavity. A small amount of plaster is added to the exposed upper surface of the sponge to seal its surface.

Figure 2:
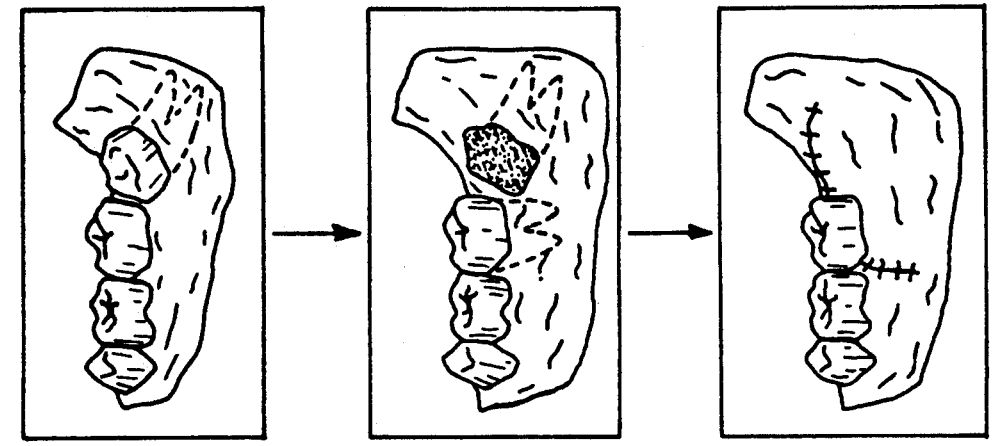
FIG. 2 is a perspective view of the area surrounding a tooth extraction site treated in accordance with the principles of the present invention.

As best seen in FIG. 2, the tissues above the plaster impregnated sponge are then sutured together to enclose it completely, thus preventing any food or debris from entering the wound site. In addition to being somewhat resilient which aids in filling the cavity, the gelatin sponge both reduces the amount of plaster required and, since the gelatin is more quickly absorbed by the body than the plaster, allows vascular ingrowth into the remaining plaster. This minimizes the opportunity for portions of the plaster to remain unabsorbed.

Small wounds may not need the gelatin sponge. In such cases the semi-liquid plaster is allowed to stand for 1 or 2 minutes in order to form a putty-like consistency. The putty-like, plaster of Paris is then used to fill the cavity formed by the extraction of a tooth or removal of a cyst. After the cavity is filled, approximately 1 or 2 minutes allows the plaster to further cure and solidify in place prior to suturing.

The method and composition of the present invention is operable to prevent the occurrence of the painful condition known as dry socket and, at the same time, is moldable to prevent unnecessary pressure at the affected site and is absorbed into the body to permit regeneration of bone in the affected area.

A more complete understanding of the present invention can be obtained by referring to the following illustrative examples of the invention, which examples are not intended to be unduly limitative of the invention. All percentages are expressed as weight percentages unless otherwise indicated.

EXAMPLE ONE

Plaster of Paris containing 0.85 wt. % potassium sulfate ($K_2SO_4$) was mixed with sterilized water at a ratio of 0.1 ml/gm of plaster and allowed to stiffen slightly before being placed in the third molar socket in the number 17 socket. The socket area was not completely filled. After 4 days the patient came back with a minor dry socket. The plaster was noted to still be in place and the dry socket was limited to the incompletely filled socket area. The dry socket was relieved with just a minor amount of eugenoal placed over the incompletely filled socket. After 40 days, X-ray examination indicated that the plaster had been substantially absorbed by the body.

EXAMPLE TWO

Plaster of Paris containing 0.85 wt. % potassium sulfate ($K_2SO_4$) was mixed with sterilized water at a ratio of 0.1 ml/gm of plaster and allowed to stiffen slightly before being placed in the third molar socket in another number 17 socket. The socket area was completely filled. The wound healed completely and without occurrence of a dry socket. After 50 days, X-ray examination indicated that the plaster had been substantially absorbed by the body.

EXAMPLE THREE

Plaster of Paris containing 0.85 wt. % potassium sulfate ($K_2SO_4$) was mixed with sterilized water at a ratio of 0.1 ml/gm of plaster and allowed to stiffen slightly before being placed in the third molar socket in both the numbers 17 and 32 sockets. The socket areas were completely filled. The wounds healed completely and without occurrence of a dry socket. After 45 days, X-ray examination indicated that the plaster had been substantially absorbed by the body.

EXAMPLE FOUR

Plaster of Paris containing 0.85 wt. % potassium sulfate ($K_2SO_4$) and the addition of 5 wt. % tetracycline and 0.01 wt. % of hydrocortisone was mixed with sterilized water at a ratio of 0.1 ml/gm of plaster and allowed to stiffen slightly before being placed in the third molar socket in the number 17 socket. The socket area was completely filled. The wound healed completely and without occurrence of a dry socket. In addition, the tetracycline and hydrocortisone appeared to have eliminated any inflammation in the area of the wound. After 65 days, X-ray examination indicated that the plaster was substantially absorbed by the body.

EXAMPLE FIVE

Plaster of Paris containing 0.5 wt. % potassium sulfate ($K_2SO_4$) and the addition of 5 wt. % tetracycline and 0.01 wt. % of hydrocortisone was mixed with sterilized water at a ratio of 0.1 ml/gm of plaster. A plug of absorbable gelatin sponge was then cut out slightly larger than the socket left by the tooth extraction. The sponge was immersed into the semi-liquid plaster to absorb as much of the plaster as possible. The impregnated sponge is then placed in the third molar socket in the number 17 socket. The socket area was completely filled. The wound healed completely and without occurrence of a dry socket. In addition, the tetracycline and hydrocortisone appeared to have eliminated any inflammation in the area of the wound. After 65 days, X-ray examination indicated that the plaster was substantially absorbed by the body.

As shown in the above examples, X-ray examination of the patients in Examples 1-3 indicated that the plaster of Paris is absorbed in between 6½ and 7 weeks. However, when plaster is used alone a small inflammation reaction at the wound site sometimes occurs. This small inflammatory reaction may be decreased considerably by mixing the composition with tetracycline and hydrocortisone (see Examples 4 and 5). Note, that the addition of the tetracycline and hydrocortisone does increase the time necessary for absorption of the plaster to between 10 and 12 weeks. The longer absorption time does not appear to result in any problems.

Certain modifications and improvements will occur to those skilled in the art and from the reading of the foregoing description. By way of example, other antibiotic compounds could be added to the plaster of Paris for similar protection against infection. It should be understood that all such modifications and improvements have been deleted herein for the sake of conciseness and readability that are properly within the scope of the following claims.

I claim:

1. A method for the prevention of alveolar osteitis following the extraction of a tooth or removal of a cyst which comprises:
   preparing a dressing of semi-liquid paste containing primarily plaster of Paris;
   packing said dressing into the cavity formed by the extraction whereby said dressing substantially fills and assumes the shape of the cavity;
   suturing the tissues above said dressing to enclose said dressing; and
   allowing said dressing to stand to form a putty-like consistency prior to packing said dressing in the cavity.

2. The method according to claim 1, further including the step of permitting the cavity to heal wherein said dressing is absorbed and permits regeneration of bone in the cavity.

3. The method according to claim 1, further including the step of allowing said packing dressing to stand to allow the dressing to further cure and solidify in the cavity prior to suturing the tissues above said dressing.

4. A method for the prevention of alveolar osteitis following the extraction of a tooth or removal of a cyst which comprises:
   preparing a semi-liquid paste containing primarily plaster of Paris;
   forming a plug of absorbant material slightly larger in size and similar in shape to the cavity formed by the extraction;
   immersing the plug into the semi-liquid paste to impregnate the plug;
   packing said impregnated plug into the cavity formed by the extraction; and
   suturing the tissues above said impregnated plug to enclose said plug.

5. The method according to claim 4, wherein said absorbant material is absorbable by the human body.

6. The method according to claim 5, wherein said absorbant material is gelatin sponge.

7. The method according to claim 4, wherein said impregnated plug is moldable for reducing pressure and aiding in filling the cavity.

8. The method according to calim 7, wherein said impregnated plug is slightly resilient for aiding in filling the cavity.

9. The method according to claim 4, further including the step of applying a small amount of plaster to the exposed upper surface of said plug to seal its surface prior to suturing.

10. The method according to claim 4, further including the step of permitting the cavity to heal wherein said impregnated plug is absorbed and permits regeneration of bone in the cavity.

11. A dressing for the prevention of alveolar osteitis following the extraction of a tooth or removal of a cyst from a body comprising:
    a semi-liquid paste of plaster of Paris having a putty-like consistency, said paste being sufficiently moldable to conform to the shape of the cavity formed by the extraction; and
    at least one active ingredient to reduce inflammation at the extraction site.

12. The dressing according to claim 11, wherein said plaster includes 0.85 wt. % $K_2SO_4$ to facilitate solidification in the body.

13. The dressing according to claim 12, further including approximately 5 wt. % tetracycline and 0.01 wt. % of hydrocortisone to reduce inflammation at the extraction site.

14. A dressing for the prevention of alveolar osteitis following the extraction of a tooth or removal of a cyst from a body comprising:
    a plug of absorbant material absorbable in the body and impregnated with semi-liquid plaster of Paris, said plug being slightly larger in size and similar in shape to the cavity formed by the extraction, said plug being sufficiently moldable to conform to the shape of the cavity formed by the extraction.

15. The dressing according to claim 14, wherein said plaster includes approximately 0.85 wt. % $K_2SO_4$ to facilitate solidification in the body.

16. The dressing according to claim 15, further including approximately 5 wt. % of tetracycline and 0.01 wt. % of hydrocortisone to reduce inflammation at the extraction site.

* * * * *